(12) United States Patent
Ostermeyer

(10) Patent No.: US 10,267,727 B2
(45) Date of Patent: Apr. 23, 2019

(54) DETERMINING POLARIZATION ROTATION CHARACTERISTICS OF A SAMPLE TAKING INTO CONSIDERATION A TRANSMISSION DISPERSION

(71) Applicant: Anton Paar Optotec GmbH, Seelze-Letter (DE)

(72) Inventor: Martin Ostermeyer, Gehrden (DE)

(73) Assignee: Anton Paar Optotec GmbH, Seelze-Letter (DE)

( * ) Notice: Subject to any disclaimer, the term of this patent is extended or adjusted under 35 U.S.C. 154(b) by 0 days.

(21) Appl. No.: 15/536,469

(22) PCT Filed: Nov. 10, 2015

(86) PCT No.: PCT/EP2015/076205
§ 371 (c)(1),
(2) Date: Jun. 15, 2017

(87) PCT Pub. No.: WO2016/096249
PCT Pub. Date: Jun. 23, 2016

(65) Prior Publication Data
US 2018/0321136 A1     Nov. 8, 2018

(30) Foreign Application Priority Data
Dec. 19, 2014   (DE) .................. 10 2014 119 235

(51) Int. Cl.
*G01N 21/21*       (2006.01)
*G01N 21/27*       (2006.01)
(Continued)

(52) U.S. Cl.
CPC .............. *G01N 21/211* (2013.01); *G01J 4/00* (2013.01); *G01N 21/21* (2013.01); *G01N 21/274* (2013.01);
(Continued)

(58) Field of Classification Search
CPC ........ G01N 21/211; G01N 21/314; G01J 4/00; G01J 4/04
See application file for complete search history.

(56) References Cited

U.S. PATENT DOCUMENTS 9,964 A      8/1853   Magoun
3,481,671 A  12/1969  West et al.
(Continued)

FOREIGN PATENT DOCUMENTS

DE    27 16 314 A1    12/1978
DE    10 001 810 B4    5/2010
(Continued)

OTHER PUBLICATIONS

M. Dubreuil et al., Snapshot Mueller matrix polarimetry by wavelength polarization coding and application to the study of switching dynamics in a ferroelectric liquid crystal cell, SPIE, PO Box 10 Bellingham WA 98227-0010, USA, vol. 7787, 2010, XP040543412, Sections 2 and 3.1.
(Continued)

*Primary Examiner* — Maurice C Smith
(74) *Attorney, Agent, or Firm* — Robert A. Blaha; Smith Tempel Blaha LLC

(57) ABSTRACT

Optical measuring system for determining polarization-optical properties of a sample, which comprises a polarization state generator (PSG) which is configured for preparing a measuring light which is propagating along an analysis beam path with a defined polarization state; a sample receptacle which is arranged downstream of the PSG in the analysis beam path and which is adapted for receiving the sample; a polarization state analyzer (PSA) which is arranged downstream of the sample receptacle in the analysis beam path; a detector which is arranged downstream of the PSA in the analysis beam path for detecting the measuring light, wherein the PSA and the detector are configured
(Continued)

for capturing a polarization rotation $\alpha_P(\lambda_{eff})$ of the measuring light which is caused by the sample; and an evaluation and control unit for evaluating measuring signals from the detector and/or PSA and/or PSG, wherein a wavelength-spectrum of the measuring light contains at least a first wavelength $\lambda_1$ and a second wavelength $\lambda_2$, wherein the detector is configured for detecting measuring light with the first wavelength separated from measuring light with the second wavelength, and wherein the evaluation and control unit is configured for calculating a polarization rotation $\alpha_P(\lambda_0)$ of the measuring light which is caused by the sample at a standardized wavelength $\lambda_0$ in dependency from (a) a first polarization rotation $\alpha_P(\lambda_1)$ at the first wavelength $\lambda_1$, (b) a second polarization rotation $\alpha_P(\lambda_2)$ at the second wavelength $\lambda_2$, (c) a first transmission $T(\lambda_1)$ at the first wavelength $\lambda_1$, and (d) a second transmission $T(\lambda_2)$ at the second wavelength $\lambda_2$.

18 Claims, 2 Drawing Sheets

(51) Int. Cl.
  *G01N 21/31* (2006.01)
  *G01J 4/00* (2006.01)
(52) U.S. Cl.
  CPC ... *G01N 21/314* (2013.01); *G01N 2021/3137* (2013.01); *G01N 2021/3148* (2013.01)

(56) References Cited

U.S. PATENT DOCUMENTS

| 4,668,086 | A | 5/1987 | Redner |
| 2009/0033936 | A1 | 2/2009 | Otani et al. |
| 2013/0169964 | A1 | 7/2013 | Wagner |

FOREIGN PATENT DOCUMENTS

| DE | 10 2011 005 807 A1 | 9/2012 |
| EP | 0 536 985 A1 | 4/1993 |
| GB | 1 603 256 A1 | 11/1981 |
| JP | 2003-172691 A1 | 6/2003 |
| JP | 3866849 B2 | 10/2006 |

OTHER PUBLICATIONS

Q. Wan et al.: "Dual-wavelength polarimetry for monitoring glucose in the presence of varying birefringence", vol. 20, No. 2, 2005, XP040213710, Section 2.

Zander, Melle Importance and realization of defined wavelengths in saccharimetry, Sugar Technology Reviews, 8,1982.

R. M. A. Azzam, "Ellipsometry", Chapter 27 in "Handbook of Optics vol. II", Michael Bass (ed.), Optical Society of America 1995.

R. A. Chipman, "Polarimetry", Chapter 22 in "Handbook of Optics vol. II", Michael Bass (ed.), Optical Society of America 1995.

DETERMINING POLARIZATION ROTATION CHARACTERISTICS OF A SAMPLE TAKING INTO CONSIDERATION A TRANSMISSION DISPERSION

CROSS-REFERENCE TO RELATED APPLICATIONS

This application is a US national phase application of international patent application PCT/EP2015/076205 filed on Nov. 10, 2015, which claims the benefit of the filing date of German Patent Application No. 10 2014 119 235.4, filed on Dec. 19, 2014, the disclosures of which are hereby incorporated herein by reference in their entirety.

TECHNICAL FIELD

Embodiments of the present invention relates to the technical field of optical measuring systems and methods for determining polarization-optical properties of a sample.

TECHNOLOGICAL BACKGROUND

Polarimeters are measuring devices which measure polarization-optical properties of samples. In particular, with a polarimeter the optical rotation of an optically active sample is measured.

The optical polarization rotation of a sample is dependent on the wavelength of the light which is radiating through the sample, which is also denoted as measuring light in the following. In this document, the term polarization rotation in short is also denoted as (optical) rotation. In order to make polarization-optical measurements comparable, the optical rotation has to be measured at a standardized wavelength. Even when the optical polarization rotation of a sample is measured correctly at the current wavelength of the polarimeter, a deviation from the desired standardized wavelength leads to a measuring error for the optical rotation which is caused by the sample. This measuring error is determined on the one hand by an error of the wavelength of the measuring light and on the other hand by the dependency of the optical rotation of the sample from the wavelength.

EP 0 536 985 A1 discloses a method for calibrating a polarimeter which, in a calibrated state, shall operate with an unknown wavelength, at a standardized wavelength. A sample shall be measured with the unknown wavelength and the parameters of the polarimeter shall be adjusted such that the measurement with the unknown wavelength results in measuring values which correspond to a measurement with the standardized wavelength.

US 2013 169964 A1 discloses a method by which, in a polarimeter, the current wavelength of a measuring light at the point in time of a polarization-optical measurement can be ascertained. For this purpose, two measurements are performed: in a first measurement, the optical rotation of the sample to be measured is determined, in the second measurement, in addition to the sample, a polarization rotator is pivoted in the beam path and thus the combined optical rotation of the sample and the polarization rotator is measured. From the difference between the polarization rotations which are obtained with both measurements, the optical rotation of the polarization rotator is obtained, measured at the current wavelength of the polarimeter. From the known wavelength dependency of the optical rotation of the polarization rotator, the current wavelength of the polarimeter can then be determined.

There may be a need to increase the accuracy for the determination of polarization-optical properties of a sample and in particular of a polarization rotation which is caused by the sample.

SUMMARY

This need is met by the subject-matters of the independent claims. Advantageous embodiments of the present invention are described in the dependent claims.

According to a first aspect of the invention, an optical measuring system for determining polarization-optical properties of a sample is described. The described optical measuring system comprises (a) a polarization state generator which is configured for preparing a measuring light which is propagating along an analysis beam path with a defined polarization state; (b) a sample receptacle which is arranged downstream of the polarization state generator in the analysis beam path and which is adapted for receiving the sample; (c) a polarization state analyzer which is arranged downstream of the sample receptacle in the analysis beam path; (d) a detector which is arranged downstream of the polarization state analyzer in the analysis beam path, for detecting an intensity of the measuring light, wherein the polarization state analyzer and the detector are configured for capturing a polarization rotation of the measuring light which is caused by the sample; and (e) an evaluation and control unit for evaluating measuring signals from the detector and/or from the polarization state analyzer and/or from the polarization state generator, wherein a wavelength-spectrum of the measuring light contains at least a first wavelength and a second wavelength. The detector is configured for detecting measuring light with the first wavelength separated from measuring light with the second wavelength. The evaluation and control unit is configured for calculating a polarization rotation of the measuring light which is caused by the sample at a standardized wavelength in dependency from (i) a first polarization rotation at the first wavelength, (ii) a second polarization rotation at the second wavelength, (iii) a first transmission at the first wavelength, and (iv) a second transmission at the second wavelength.

The described optical measuring system is based on the knowledge that a different transmission and absorption, respectively, of the measuring light at different light wavelengths and light frequencies, respectively, i.e. a transmission dispersion and absorption dispersion, respectively, also has an influence on the polarization rotation which is measured by the optical measuring system which is configured as polarimeter. In this context, it is easy to understand that (a) in the case of an unequal attenuation of different components of the measuring light and (b) in the case of a presence of a rotation dispersion during the measurement of the polarization rotation, an unequal weighting of different wavelength components and frequency components, respectively, of the measuring light occurs. The unequal weighting then leads to a systematic measuring error which, in particular in high precision measuring applications, is so strong that a corresponding measuring value for a polarization dispersion is not reliable.

According to the embodiments of the invention, the transmission dispersion through the sample is determined by (at least) two measurements which is determined by two measurements on two measuring channels which are separated on the frequency scale and the wavelength scale, respectively. For each measuring channel, two intensity measurements can be performed, wherein the polarization state analyzer is respectively adjusted to a maximum transmission of measuring light. The first measurement takes place without a sample and the other measurement takes place with the sample. The transmission for the respective wavelength which can also be denoted as measuring wavelength is then determined by the ratio between the measured intensity with the sample and the measured intensity without a sample. The both measurements without a sample may also be performed by way of a calibration of the optical measuring system and the corresponding measuring values can be used for a multiplicity of different sample measurements.

The relation between the transmission T and the absorption A results in a known manner from the following equation T=1−A.

According to embodiments of the invention, the transmission dispersion which is determined by two corresponding measuring points (on respectively one measuring channel) is further used for calculating the polarization rotation of the measuring light which is caused by the sample at the standardized wavelength at least in dependency from the determined transmission dispersion. This means, with the described optical measuring system, firstly the transmission dispersion of the sample is determined. Subsequently, the transmission dispersion together with two values for the polarization rotation which respectively are assigned to one of the both measuring channels is used for the calculation of the polarization rotation of the measuring light which is caused by the sample, at the standardized wavelength.

It should be noted that, dependent on the concrete application, the both values for the polarization rotation can be measured by the optical measuring system or can also be provided as known. In the case of an unknown sample, the corresponding polarization rotations are measured. In the case of a known sample, for example a reference-sample which is used for a calibration, the corresponding polarization rotations may also be known (with a high accuracy) and thus do not have to be measured.

The described optical measuring system has the advantage that it can be realized based on already known optical measuring systems by means of a comparably simple modification without an extensive instrumental reconstruction. For this purpose it is only required (a) to provide two spectrally different measuring channels and/or two measuring channels which are spectrally separated from each other and (b) to program an evaluation and control unit such that the inventive calculation of the polarization rotation of the measuring light which is caused by the sample is performed at a standardized wavelength.

The described optical measuring system can be used in particular in the technical fields of polarimetry and ellipsometry. In the first case, the optical measuring system is a polarimeter, and the second case it is an ellipsometer. If the described measuring system is an ellipsometer, the relations which are described in this document with respect to the transmission of the measuring light apply with respect to the absorption of the measuring light at the respective surface of the sample.

In this document, the term "measuring light" denotes each type of electromagnetic radiation which is capable of interacting with a polarization-optical sample in a manner that, when passing through the sample or, where applicable, when reflecting at the sample, the polarization of the electromagnetic radiation is changing. The measuring light may comprise a certain bandwidth of electromagnetic radiation with different wavelengths. The measuring light may comprise radiation in arbitrary visible and invisible spectral ranges. Preferably, the measuring light is visible for the human eye.

However, the measuring light may also be infrared or ultraviolet measuring light. Of course, the type of the used optical components of the described optical measuring system should be adapted to the spectrum of the measuring light. Therefore, the term "optic" or "optical" is to be broadly interpreted and is not limited to the spectral range which is visible for the human eye.

In this document, the term "downstream" denotes the direction along the optical axis of the analysis beam path, along which direction the measuring light in the optical measuring system is propagating.

According to an embodiment of the invention, the wavelength-spectrum of the measuring light further contains at least a third wavelength. In addition, the detector is configured for detecting measuring light with the third wavelength separated from measuring light with the second wavelength and from measuring light with the first wavelength. In addition, the evaluation and control unit is further configured for calculating the polarization rotation of the measuring light which is caused by the sample at the standardized wavelength, further in dependency from (i) a third polarization rotation at the third wavelength, and (ii) a third transmission of the sample at the third wavelength.

Using and/or considering more than two wavelengths allows to approximate the rotation dispersion of the sample to be measured with an especially high accuracy in an advantageous manner. Thus, the rotation dispersion cannot only be approximated by a linear curve. Rather, also polynomials of a higher order can be used for a corresponding more accurate approximation. In this context, it is apparent for those skilled in the art that the order of a polynomial is dependent on the number of the available wavelengths. Of course, dependent on an expected course of the rotation dispersion, besides polynomials, also other functions can be used for a suitable approximation of the rotation dispersion.

According to a further embodiment of the invention, the optical measuring system further comprises a light source which is adapted for sending the measuring light along the analysis beam path.

Thus, the described optical measuring system constitutes an autarkic measuring device which is not dependent from the provision of measuring light by an external light source. The optical measuring system therefore can be realized as a compact unit which can be used in different ambient conditions for measuring a polarization rotation of a sample.

The light source and the PSG may also be realized by a common optical component. Such a common optical component may be a laser, for example, which already sends out a linearly polarized laser light which constitutes the measuring light with the defined polarization state.

According to a further embodiment of the invention, a wavelength difference between the first wavelength and the second wavelength is smaller than 30 nm, in particular smaller than 10 nm and further in particular smaller than 1 nm. Descriptively speaking, the both wavelengths are relatively close to each other on the wavelength scale. Thereby, the course of the transmission dispersion can be approximated in a linear manner, i.e. by a straight line and/or by a polynomial of the first order in the relevant wavelength range without major errors. Such a linear approximation of the transmission dispersion has the advantage that the polarization rotation of the measuring light which is caused by the sample at the standardized wavelength can be calculated in a simple manner. Thereby, the requirements for the evaluation and control unit with respect to its available computing power are significantly reduced. The evaluation and control unit then can be realized with a processor which is comparably weak with respect to its performance and which is therefore cost-efficient.

According to a further embodiment of the invention, the evaluation and control unit is further configured for calculating the polarization rotation of the measuring light which is caused by the sample at the standardized wavelength based on (a) a first shift of a center-of-gravity-wavelength of the measuring light due to a wavelength-dependency of the transmission of measuring light through the sample, (b) a second shift of the center-of-gravity-wavelength of the measuring light due to a wavelength-dependency of a transmission of measuring light through an entirety of the optical components of the optical measuring system and (c) the first polarization rotation and the second polarization rotation.

The described calculation of the polarization rotation of the measuring light which is caused by the sample at the standardized wavelength based on the two mentioned optical shifts has the advantage that different physical causes for respectively one contribution to the measuring error with respect to the measured polarization rotation can be considered separately from each other in the calculation of the actual polarization rotation which is caused by the sample. Thus, the evaluation and control unit is capable for calculating the actual polarization rotation which is caused by the sample based on analytic equations, such that a high accuracy in the calculation of the polarization rotation which is exclusively caused by the sample results in an advantageous manner.

The first shift may be ascertained in dependency from the first transmission and the second transmission.

The mentioned second shift is often denoted as statistic wavelength error of the optical measuring system.

Within the frame of a calibration of the optical measuring system using a reference sample which has exactly known optical properties, in particular with respect to the transmission and/or absorption of electromagnetic radiation at different wavelengths, the influence of all optical components of the described measuring system with respect to their transmission dispersion can be ascertained and considered for the determination of the second shift. In this manner, an especially high measuring accuracy for the optical measuring system is achieved.

A suitable reference sample may be an optical element made of quartz and in particular a so-called quartz-control plate, for example, which can be used in a known manner for a calibration of a polarimeter. A reference sample made of quartz moreover has the advantage that quartz is optically active with respect to a polarization rotation and can also be used for a calibration of the described optical measuring system with respect to a measurement of polarization rotations.

According to a further embodiment of the invention, the evaluation and control unit is further configured for calculating the polarization rotation of the measuring light which is caused by the sample at the standardized wavelength, further based on (a) a polarization rotation which is caused by the sample at an effective wavelength which is determined by the optical properties of the entirety of the optical components of the optical measuring system and by the optical properties of the sample, and (b) an optical rotation dispersion which is caused by the sample and which is pre-known, at the standardized wavelength. This enables in a simple manner an especially accurate calculation of the polarization rotation of the measuring light which is caused by the sample at the standardized wavelength.

In this context it should be noted that the effective wavelength firstly is dependent from the wavelength and/or the wavelength spectrum of the measuring light which is emitted by the light source. As already explained above, this wavelength spectrum is modified by the transmission dispersion of all optical components and by the sample which are located in the analysis beam path.

According to a further embodiment of the invention, the optical rotation dispersion which is caused by the sample at the standardized wavelength is determined by the quotient of the difference between the first polarization rotation and the second polarization rotation and the wavelength difference between the first wavelength and the second wavelength. This means that the rotation dispersion is approximated by a simple straight line and in a linear manner, respectively. Thus, also the optical rotation dispersion which is caused by the sample at the standardized wavelength can be calculated by the evaluation and control unit in a computationally especially simple manner.

According to a further embodiment of the invention, the evaluation and control unit is further configured for determining the first shift based on a relative transmission dispersion of the sample and a proportionality factor, wherein (a) the relative transmission dispersion of the sample is given by the quotient of the transmission dispersion of the sample and the transmission of the sample and (b) the proportionality factor is specific for the transmission dispersion of the entirety of the optical components and in particular is determinable by means of an optical calibration of the optical measuring system using a reference sample.

In particular, the first shift may be determined by means of a multiplication of the mentioned relative transmission dispersion and the mentioned device-specific proportionality factor. Thus, the calculation effort for the calculation of the polarization rotation which is caused by the sample at the standardized wavelength is especially low. Consequently, the described evaluation and control unit can be already realized with a very simple and thus also very cost-efficient processor.

Also the proportionality factor can be ascertained from a measurement of a suitable reference sample in the frame of an above described calibration of the optical measuring system.

According to a further embodiment of the invention, the relative transmission dispersion of the sample is determined by the quotient of (a) the difference between the first transmission and the second transmission and (b) the product of the sum of the first transmission and the second transmission and the wavelength difference between the first wavelength and the second wavelength. Thereby, the relative transmission dispersion is determined in a computationally simple manner by a linear approximation of the measured transmissions at the both wavelengths.

According to a further embodiment of the invention, the optical measuring system further comprises a switchable optical filter device which is located in the analysis beam path and which is adapted for determining an operational state of the optical measuring system to the effect that in a first operational state only measuring light with the first wavelength and in a second operational state only measuring light with the second wavelength reaches the detector.

Descriptively speaking, the described switchable optical filter device can ensure that the detector alternately captures (a) the intensity of the first part of the spectrum of the measuring light, which first part is assigned to the first wavelength, and (b) the intensity of a second part of the spectrum of the measuring light, which second part is assigned to the second wavelength.

In this context it should be noted that, in the case that multiple wavelengths and measuring wavelengths, respectively, are used, also the switchable optical filter device has to be adapted for selecting further wavelengths in further operational states.

According to a further embodiment of the invention, the switchable optical filter device comprises a first optical filter which is assigned to the first wavelength and a second optical filter which is assigned to the second wavelength. The switchable optical filter device is further configured for arranging the first optical filter in the analysis beam path in the first operational state and for arranging the second optical filter in the analysis beam path in the second operational state.

The both optical filters of the switchable optical filter device may be arranged at a wheel which is rotatably mounted, such that by a simple rotation of the wheel, the optical measuring system can be switched between the both operational states. Such a wheel which is equipped with different filters is also often denoted as filter wheel.

The both optical filters may alternatively be attached to a linearly slidable frame, such that by means of a corresponding translational shift of the frame, in particular by means of a linear drive, the optical measuring system can be switched between the both operational states.

For the both filters, in principle arbitrary types of optical filters and in particular narrowband bandpass filters can be used. Typical bandwidths are narrower than 30 nm, preferably narrower than 10 nm and further preferably narrower than 5 nm. In particular, interference filters and/or combinations of multiple filters, such as edge filters, are suitable.

At this point it should be noted that the operation of the switchable optical filter device should be controlled by the evaluation and control unit. Thereby, the evaluation and control unit can unambiguously assign the different measuring signals which are generated by the detector to the different operational states. This constitutes an important precondition in order to enable the evaluation and control unit to calculate the polarization rotation of the measuring light which is caused by the sample at the standardized wavelength, as described above.

According to a further embodiment of the invention, the switchable optical filter device comprises (a) an optical filter which is arranged in the analysis beam path, and (b) an actuator which is adapted for varying an angular position of the optical filter between a first angle which is assigned to the first operational state and a second angle which is assigned to the second operational state.

This embodiment is based on the fact that the optical thickness of the filter which is relevant for the measuring light changes by a change of the angular position of the filter. The more slanting the filter is arranged in the analysis beam path, the larger is the optical thickness. Since the optical thickness at least at interference filters is relevant for their spectral filter properties, by a simple tilting motion, the wavelength and the wavelength range, respectively, of the measuring light which impinges on the detector can be adjusted.

The described actuator may be an arbitrary rotary drive which is mechanically coupled to the optical filter in a suitable manner. However, the actuator may also be a linear drive which is mechanically coupled to an element which is pivotable around a rotary axis, to which element the optical filter is directly or indirectly attached. For a high positioning accuracy, the actuator may be a piezo-actuator.

According to a further embodiment of the invention, the optical measuring system further comprises a beam splitter which is arranged downstream of the sample in the analysis beam path and which is configured for splitting the measuring light into a first partial beam and into a second partial beam, wherein the first partial beam is assigned to the first wavelength and the second partial beam is assigned to the second wavelength. The detector further comprises two detector elements, wherein a first detector element is assigned to the first wavelength and the second detector element is assigned to the second wavelength.

The described beam splitter may be a simple beam splitter which splits the measuring light uniformly, such that both partial beams comprise the same wavelength spectrum at least directly after the beam splitter. In order to achieve a wavelength selectivity of the both measuring channels which respectively are assigned to a wavelength, a suitable filter, in particular an interference filter with a very low bandwidth, can be assigned to each detector element.

It should be noted that instead of or in combination with such optical filters also a wavelength selective beam splitter may be used.

The described splitting of the measuring beam into two partial beams which are spatially separated from each other, whose intensity is respectively captured by a detector element, has the advantage that simultaneously in both measuring channels corresponding intensity measurements can be performed. A further advantage of the here described embodiment may be seen in that the optical measuring system can be realized with no or with only a very low number of mechanically movable components. Thereby, the mechanical robustness of the optical measuring system can be increased and the lifetime of the optical measuring system can be prolonged in an advantageous manner.

According to a further embodiment of the invention, the optical measuring system further comprises a spectrally resolving optical element which together with the detector forms a part of a spectrometer.

In connection with the here described optical measuring system, the spectrometer can take over both the function of a wavelength selector and the function of the detector. However, in particular for an above described embodiment in which the both wavelengths are close to each other, the spectrometer has to comprise a sufficient spectral resolution. In this context, the spectrally resolving optical element may be a light refractive prism or a light deflective grating.

For a high stability of the optical measuring system which is required for many applications, a good reproducibility of the spectral resolution is further required. This may in particular be achieved by a spectrometer which, at least for achieving the required spectral resolution, comprises no movable components. Such a spectrometer may be a known monolithic array-spectrometer, for example, which enables a time-saving simultaneous measurement of the both wavelengths in an advantageous manner.

According to a further aspect of the invention, a method of determining polarization-optical properties of a sample, in particular using the above-described optical measuring system, is described. The described method comprises (a) preparing, by means of a polarization state generator, a measuring light which is propagating along an analysis beam path with a defined polarization state; (b) directing the measuring light to a sample which is located downstream of the polarization state generator in the analysis beam path; (c) capturing a polarization rotation of the measuring light which is caused by the sample (i) by means of a polarization state analyzer which is arranged downstream of the sample in the analysis beam path, and (ii) by means of a detector which is arranged downstream of the polarization state analyzer in the analysis beam path, wherein a wavelength-spectrum of the measuring light contains at least a first wavelength and a second wavelength and wherein the detector is detecting measuring light with the first wavelength separated from measuring light with the second wavelength; and (d) evaluating measuring signals from the detector and/or from the polarization state analyzer and/or from the polarization state generator by means of an evaluation and control unit, wherein a polarization rotation of the measuring light which is caused by the sample at a standardized wavelength is calculated in dependency from (i) a first polarization rotation at the first wavelength, (ii) a second polarization rotation at the second wavelength, (iii) a first transmission at the first wavelength, and (iv) a second transmission at the second wavelength.

Also the described method is based on the knowledge that at least two measuring channels which are spaced with respect to each other on the frequency axis can be used for calculating a transmission dispersion and/or an absorption dispersion which is caused by the sample and, based on this information, for correcting a measuring value for the polarization rotation of the sample, which measuring value is ascertained by the detector together with the polarization state analyzer and which measuring value is at least slightly erroneous, in a suitable manner, such that a polarization rotation of the measuring light which is caused by the sample at a standardized wavelength results with a high accuracy.

According to an embodiment of the invention, the method further comprises (a) determining the first transmission (in a first measuring channel) by a comparison of a first intensity which is measured by the detector and a further first intensity which is measured by the detector, wherein the first intensity results from a measurement without a sample and the further first intensity results from a measurement with the sample; and (b) determining the second transmission (in a second measuring channel) by a comparison of a second intensity which is measured by the detector and a further second intensity which is measured by the detector, wherein the second intensity results from a measurement without a sample and the further second intensity results from a measurement with the sample. Thereby, the both transmissions which are required for the calculation of the polarization rotation which is caused by the sample at the standardized wavelength can be determined in an especially simple manner.

According to a further embodiment of the invention, the method further comprises (a) determining the first polarization rotation (in the first measuring channel) by a comparison between a captured first polarization state and a captured further first polarization state, wherein the first polarization state results from a measurement without a sample and the further first polarization state results from a measurement with the sample; and (b) determining the second polarization rotation (in the second measuring channel) by a comparison between a captured second polarization state and a captured further second polarization state, wherein the second polarization state results from a measurement without a sample and the further second polarization state results from a measurement with the sample. Thereby, also the both polarization rotations which are required for the calculation of the polarization rotation which is caused by an unknown sample at the standardized wavelength can be determined in an especially simple manner.

The mentioned polarization states of the measuring light may be respectively captured by the detector and/or by the polarization state analyzer in a known manner and may be determined by the evaluation and control unit.

It should be noted that the described determining of the both polarization rotations by means of concrete experimental measurements is not required if the sample is a sample, in particular a reference sample, with known rotation-optical properties. In other words, in contrast to the above described experimental determination of the both transmissions which is mandatory for performing the here described method, the here described experimental determining of the polarization dispersion based on the both polarization-rotations can be omitted when measuring known polarization-optical active (reference) samples. The known rotation dispersion of diverse samples may be stored in a storage medium and used for calculating the polarization rotation of the measuring light which is caused by the sample. Alternatively, the corresponding values may also be input in the optical measuring system by a user via an interface.

It should be noted that the optical measuring system which is described in this document may also be equipped with more than two measuring channels. A configuration with three or more measuring channels would have the advantage that the polarization rotation of the measuring light which is caused by the sample could be calculated at the standardized wavelength with an even higher accuracy.

According to a further aspect of the invention, a computer program for determining polarization-optical properties of a sample, in particular using the above-described optical measuring system, is described. The computer program, when it is executed by an evaluation and control unit, in connection with a polarization state generator, a sample receptacle, a polarization state analyzer and a detector is adapted for performing the above described method.

In terms of this document, the mention of such a computer program is equivalent to the term of a program-element, a computer program product and/or a computer readable medium which receives instructions for controlling a computer system, in order to coordinate the operation of an optical measuring system in a suitable manner, in order to achieve the effects which are associated with the inventive method. The computer program may be implemented as computer readable instruction code in each suitable programming language, such as JAVA, C++, C, C# or MATLAB. The computer program may be stored on a computer readable storage medium (CD-ROM, DVD, blue-Ray disc, removable drive, volatile or non-volatile storage, built-in storage/processor etc.). The instruction code can program a computer or other programmable devices, such that the desired functions are performed. Furthermore, the computer program may be provided in a network, such as the Internet, from which it can be downloaded by a user when required.

It should be noted that embodiments of the invention are described with reference to different subject-matters of the invention. In particular, some embodiments of the invention are described with apparatus claims and other embodiments of the invention are described with method claims. When reading this application, it becomes immediately apparent to those skilled in the art that, unless explicitly otherwise specified, in addition to a combination of features which belong to a type of subject-matter of the invention, also an arbitrary combination of features is possible which belong to different types of subject-matters of the invention.

Further advantages and features of the embodiments of the present invention can be taken from the following exemplary description of currently preferred embodiments.

The single figures of the drawing of this application are to be considered as merely schematically and not as true to scale.

DETAILED DESCRIPTION OF EXEMPLARY EMBODIMENTS

Figure 1:
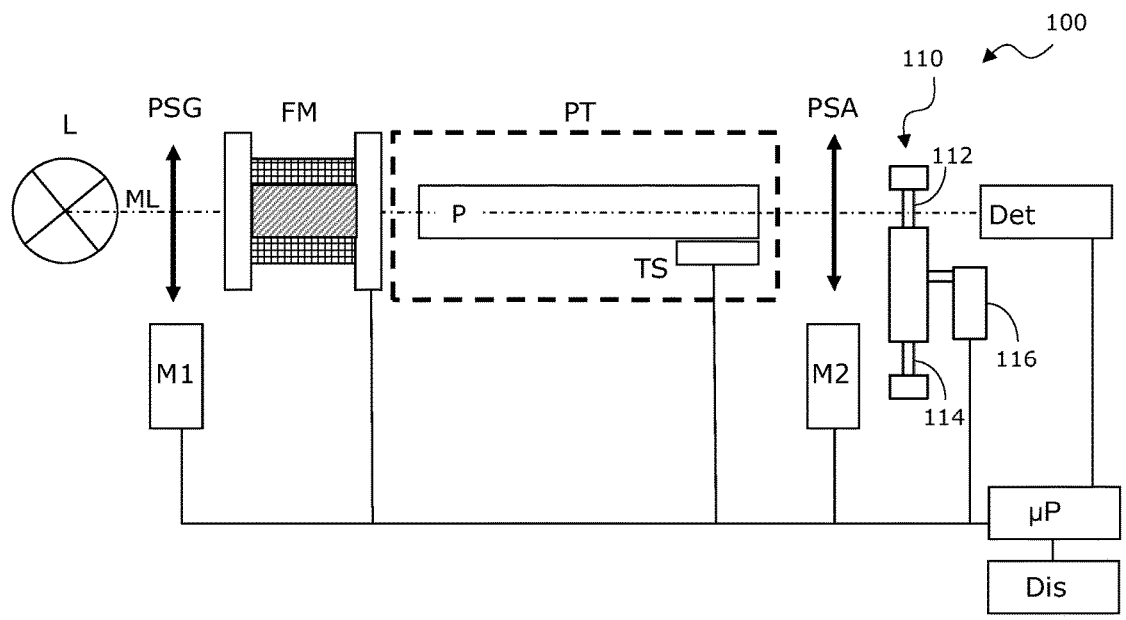
FIG. 1 shows an optical measuring system which is configured as a polarimeter, wherein two measuring channels are realized by a rotatable wheel to which two interference filters which are configured as bandpass filters are attached.

It should be noted that in the following detailed description, features and components, respectively, of different embodiments which are equal or at least functionally equal to the respective features and components, respectively, of another embodiment, are provided with the same reference signs or with a reference sign which only differs in the first digit from the reference sign of the equal or at least functionally equal features and components, respectively. In order to avoid unnecessary repetitions, features and components, respectively, which have been already described by means of a previously described embodiment, shall not be described in detail later.

Further, it should be noted that the subsequently described embodiments merely constitute a restricted selection of possible variants of the embodiments of the invention. In particular, it is possible to combine the features of the single embodiments in a suitable manner, such that with the variants of the embodiments which are explicitly shown here, a multiplicity of different embodiments are to be considered as obviously disclosed for those skilled in the art.

For sake of a better understanding of the embodiments of the invention, some technical and/or mathematical basics are described below on which embodiments of the present invention are based.

Ideally, polarimetric measurements should be performed with monochromatic light at a standardized wavelength $\lambda_0$. However, the most commercial polarimeters use broadband incoherent light sources, such as tungsten halogen lamps or LEDs. The wavelength which may also be denoted as measuring wavelength is then adjusted by suitable wavelength selectors. Real wavelength selectors have to comprise a finite bandwidth, in order that enough light is available for the measurement. Preferred spectral bandwidths are in a range from 5 to 10 nm (full width at half maximum). Within this restricted spectral range, the relevant effective wavelength $\lambda_{eff}$ results.

The effective wavelength $\lambda_{eff}$ is the center-of-gravity wavelength of the effective spectrum $W(\lambda)$ of the polarimetric measurement. The effective spectrum $W(\lambda)$ summarizes the consequence of all wavelength-dependent effects which are influencing the measurement. These typically include the emission spectrum of the light source, the spectrum of the sensitivity of the detector, the transmission spectrum of the wavelength selector, and other effects which are specific for the measuring principle of the polarimeter, such as the wavelength-dependent modulation amplitude of a Faraday-modulator.

The above mentioned contributions to the effective spectrum $W(\lambda)$ are device-specific and can also be summarized in a so-called device function $G(\lambda)$. However, in general, the effective spectrum $W(\lambda)$ is also influenced by a wavelength-transmission or sample transmission $T(\lambda)$ of a sample which is introduced in the beam path of the polarimeter. Thus, the effective spectrum $W(\lambda)$ is the product of the device function $G(\lambda)$ and the sample transmission $T(\lambda)$. The effective wavelength therefore is:

$$\lambda_{eff} = \frac{\int_{\lambda_1}^{\lambda_2} G(\lambda)T(\lambda)\lambda d\lambda}{\int_{\lambda_1}^{\lambda_2} G(\lambda)T(\lambda)d\lambda} \quad (1)$$

$\lambda_1$ and $\lambda_2$ specify the limits of the spectral range which is restricted by the wavelength selective elements.

In samples whose transmission is constant within a restricted spectral range ($T(\lambda)$=const., no transmission dispersion), the sample does not have an influence on the center-of-gravity wavelength, and the effective wavelength $\lambda_{eff}$ is equal to the center-of-gravity wavelength of the device function $G(\lambda)$ and is denoted as wavelength of the device $\lambda_G$ in the following:

$$\lambda_G = \frac{\int_{\lambda_1}^{\lambda_2} G(\lambda)\lambda d\lambda}{\int_{\lambda_1}^{\lambda_2} G(\lambda)d\lambda} \quad (2)$$

This in particular applies for transparent samples ($T(\lambda)$=1) and thus also for quartz-control plates which are usually used for calibration purposes as polarization-optically active reference samples. When using stable wavelength selectors, a setting of the wavelength of the device can be performed in a known manner by an adjustment using a quartz-control plate. The adjusted wavelength then is maintained between subsequent measurements.

In colored samples, i.e. in samples whose transmission $T(\lambda)$ changes due to absorption or scattering within the restricted spectral range (the transmission dispersion $T'(\lambda)$= $dT/d\lambda$ is unequal to zero), the sample conversely has, according to equation (1), an influence on the effective wavelength $\lambda_{eff}$ which is therefore no longer equal to the wavelength $\lambda_G$ of the device. This means that the effective wavelength $\lambda_{eff}$ may change from sample to sample, namely due to a wavelength error which is generated by the sample itself due to its transmission dispersion $T'(\lambda)$.

In general, the error $\Delta\lambda_P(T')$ by colored samples can be defined only as difference between the effective wavelength $\lambda_{eff}$ with the sample and the wavelength $\lambda_G$ of the device (without the sample):

$$\Delta\lambda_P(T')=\lambda_{eff}-\lambda_G$$

When the relevant wavelength interval $\lambda_1 \ldots \lambda_2$ is narrow enough, the course of the sample transmission can be linearly approximated.

For the general device function $G(\lambda)$, there is a proportionality to the relative transmission dispersion $T'/T$ of the sample:

$$\Delta\lambda_P(T')=\kappa*T'/T \quad (3)$$

The proportionality factor κ (kappa) is determined by the exact shape of the device function G(λ), wherein in particular the effective width of the device function G(λ) is important.

It can be seen that the absolute value of the transmission of the sample at the effective wavelength $\lambda_{eff}$ is not the relevant point for the wavelength change, but the relative slope of the transmission. A maximum influence of the sample transmission on the wavelength occurs when the wavelength of the device is located on an absorption edge of the sample.

The wavelength error Δλ which is relevant for the practical measurement is the deviation of the effective wavelength $\lambda_{eff}$ with the sample with respect to the standardized wavelength $\lambda_0$. It applies:

$$\Delta\lambda = \lambda_{eff} - \lambda_0 = \Delta\lambda_G + \Delta\lambda_P(T)$$

In this respect, $\Delta\lambda_G = \lambda_G - \lambda_0$ is the wavelength error of the device (without the sample), such as it results from a typical calibration with a quartz-plate.

The measuring value of a sample is the value of the optical rotation (α=alpha) at the effective wavelength of the combination of the device and the sample, therefore the value $\alpha_P(\lambda_{eff})$. However, the value $\alpha_P(\lambda_0)$ at the standardized wavelength $\lambda_0$ is searched. If the wavelength error Δλ is small enough, a linear approximation leads to the following equation:

$$\alpha_P(\lambda_{eff}) = \alpha_P(\lambda_0) + \alpha'_P(\lambda_0) * \Delta\lambda$$

In this respect, $\alpha'_P(\lambda_0) = d\alpha_P/d\lambda$ is the optical rotation dispersion of the sample, therefore the wavelength-dependent deviation of the optical rotation of the sample.

The measuring error of the optical rotation $$\Delta\alpha = \alpha_P(\lambda_{eff}) - \alpha_P(\lambda_0)$$

is proportional to both the rotation dispersion of the sample and also to the wavelength error during the measurement. In summary, therefore the following equation results:

$$\alpha_P(\lambda_0) = \alpha_P(\lambda_{eff}) - \alpha'_P(\lambda_0) * [\Delta\lambda_G + \Delta\lambda_P(T)] \quad (4)$$

As can be taken from the following description of embodiments of the invention, by means of embodiments of the invention which is described in this document, errors in polarimetric measurements can be corrected and/or compensated which are caused by a wavelength-dependent absorption and/or transmission of the sample.

In this document it is now described how the above described analysis can be used for correcting and compensating, respectively, the wavelength error of the optical rotation by means of a direct measurement, which measuring error results from both a wavelength-dependent transmission of the sample and also from a rotation dispersion of the sample.

A combination of the equations (3) and (4) results to:

$$\alpha_P(\lambda_0) = \alpha_P(\lambda_{eff}) - \alpha'_P(\lambda_0) * [\Delta\lambda_G + \kappa * T'/T] \quad (5)$$

In order to correct the error by means of this combination, the following quantities therefore have to be known:
1. The (statistical) wavelength error of the device $\Delta\lambda_G$. This can be determined by means of a conventional quartz-calibration.
2. The proportionality factor κ. This can be determined by means of a calibration.
3. The relative transmission dispersion T'/T of the sample to be measured. This transmission dispersion T'/T has to be measured.
4. The optical rotation dispersion $\alpha'_P(\lambda_0)$ of the sample: this either has to be known or it has to be measured.

The quantities 1 and 2 are calibrations of the device. They can be performed previously to sample measurements. The calibration of κ can be performed by a colored optically active reference sample.

The quantity 3 (relative transmission dispersion T'/T) has to be determined for each sample. For this purpose, according to the here described embodiment, the transmission is measured at at least two wavelengths. For this purpose, the used polarimeter has to comprise two measuring channels which are different on the wavelength scale.

The quantity 4 (optical rotation dispersion $\alpha'_P(\lambda_0)$) may be known in known sample types, such as sugar, and does not have to be measured for each single sample. In unknown samples, the optical rotation dispersion has to be measured by measuring at least two wavelengths. However, since the determination of the quantity 3 (relative transmission dispersion T'/T) anyway requires measurements at at least two wavelengths, the quantity 4 (optical rotation dispersion $\alpha'_P(\lambda_0)$) in many embodiments of the invention can be advantageously measured without additional effort.

In the following, it is now described in detail how, according to the here described embodiment, the quantity 3 (relative transmission dispersion T'/T) and the quantity 4 (optical rotation dispersion $\alpha'_P(\lambda_0)$) are measured in a simple manner.

Both in the calibration of the proportionality factor κ (kappa) and also in measuring a sample, the relative transmission dispersion T'/T and generally also the optical rotation dispersion $\alpha'_P(\lambda_0)$ have to be measured. Both quantities are defined as derivations with respect to the wavelength. However, according to the here described embodiment, they are determined as difference quotient from measurements at at least two wavelengths. The following description for the sake of simplicity is restricted to two wavelengths.

At each wavelength, both the sample transmission, thus T(λ1) and T(λ2), and also the optical rotation of the sample, thus $\alpha'_P(\lambda_1)$ and $\alpha'_P(\lambda_2)$, are measured and the quantities 3 and 4 are calculated therefrom.

For the quantity 3 (relative transmission dispersion T'/T) results:

$$\frac{T'}{T} = 2 * \frac{T(\lambda_1) - T(\lambda_2)}{(T(\lambda_1) + T(\lambda_2)) * (\lambda_1 - \lambda_2)} \quad (6)$$

For the quantity 4 (optical rotation dispersion $\alpha'_P(\lambda_0)$) results:

$$\alpha'_P(\lambda_0) = \frac{\alpha_P(\lambda_1) - \alpha_P(\lambda_2)}{\lambda_1 - \lambda_2} \quad (7)$$

The exact values of the both wavelengths $\lambda_1$ and $\lambda_2$ are not known, since they are subject to the sample-dependent wavelength error themselves. However, in this context it should be considered that the both wavelengths $\lambda_1$ and $\lambda_2$ are located so closely together, that the relative transmission dispersion T'/T in this range can be considered as being constant. The device function G(λ) of the wavelength selectors and thus the respective statistical wavelength error $\Delta\lambda_G$ and the proportionality factor κ1 for the wavelength $\lambda_1$ and the proportionality factor $\kappa_2$ for the wavelength $\lambda_2$ may be different for the both wavelengths $\lambda_1$ and $\lambda_2$. Therefore, preferably both proportionality factors $\kappa_i$ (i=1, 2; for both wavelengths $\lambda_1$ and $\lambda_2$) can be calibrated with a colored optically active reference sample (as described below) and further, the both statistical wavelength errors $\Delta\lambda_{Gi}$ (i=1, 2; for both wavelengths $\lambda_1$ and $\lambda_2$) can be determined by a normal calibration with a quartz-plate.

The exact values of the wavelengths $\lambda_1$ and $\lambda_2$ can then be iteratively determined as follows: assuming undisturbed wavelengths, by means of equation (6), a first approximation of the relative transmission dispersion T'/T is determined. Thereby, by means of equation (3), the sample-dependent wavelength errors for the both wavelengths $\lambda_1$ and $\lambda_2$ are determined. Based on these wavelength errors, the wavelengths $\lambda_1$ and $\lambda_2$ are corrected and by means of equation (6), the relative transmission dispersions T'/T in turn are determined more accurately. This mathematical procedure may be repeated, if necessary. Then, by means of the thus corrected wavelengths $\lambda_1$ and $\lambda_2$, also the optical rotation dispersion $\alpha'_P(\lambda_0)$ is determined which in turn is constantly approximated for both wavelengths.

In the following it is now described in detail how, according to the here described embodiment, the corrected measuring value $\alpha'_P(\lambda_0)$ for the polarization rotation of the sample to be measured at the standardized wavelength $\lambda_0$ is determined.

From the single measurements for both wavelengths $\lambda_1$ and $\lambda_2$, by means of equation (5), respectively one measuring value of the sample can be calculated. It is reasonable to average both measuring values.

In this respect, it should be noted that the above ascertained values for the relative transmission dispersion T'/T and the optical rotation dispersion $\alpha'_P(\lambda_0)$ apply for both wavelengths $\lambda_1$ and $\lambda_2$, but the statistical wavelength error $\Delta\lambda_{Gi}$ (i=1, 2; for both wavelengths $\lambda_1$ and $\lambda_2$) and the respective proportionality factor $\kappa_i$ can be different for both wavelengths $\lambda_1$ and $\lambda_2$. Thus, from equation (5) explicitly results:

$$\alpha_P(\lambda_0) = \frac{1}{2} * \left\{ \alpha_P(\lambda_1) + \alpha_P(\lambda_2) - \alpha'_P(\lambda_0) * \left[ \Delta\lambda_{G1} + \Delta\lambda_{G2} + (\kappa_1 + \kappa_2) * \frac{T'}{T} \right] \right\}$$

In the following it is now described in detail how, according to the here described embodiment, the proportionality factor $\kappa$ and/or the proportionality factors $\kappa_i$ are determined.

For this purpose, a colored optically active reference sample is used whose optical rotation and optical rotation dispersion and whose relative transmission dispersion at the standardized wavelength $\lambda_0$ are known. Such a reference sample may be simply manufactured by a combination of a normal quartz-plate and a suitable filter, for example. The optical rotation of the quartz-plate is determined separately, thus without the colored filter, as in a normal calibration in a polarimeter. The optical rotation dispersion of quartz is known from literature (see for example http://www.icumsa.org/ or http://www.oiml.org/fr). The relative transmission dispersion of the colored filter is determined separately, thus without the quartz-plate, in a spectrometer. For this purpose, the optical rotation of the colored filter (without a quartz-plate) is determined.

A measurement of such a reference sample in a polarimeter to be calibrated results in a deviation $\Delta\alpha$ of the measured optical rotation from the known reference value. The optical rotation dispersion of the reference sample and its relative transmission dispersion are known. The wavelength error of the device $\Delta\lambda_G$ is determined by a previous normal quartz-calibration. Then, by means of equation (5), the proportionality factor $\kappa$ and the both proportionality factors $\kappa_i$, respectively, can be determined.

In this context, it is assumed that the reference sample at the wavelengths of interest comprises an optical rotation dispersion and causes a change in absorption. Alternatively to the above-mentioned example, the reference sample may comprise a quartz-plate and a colored solution, an optically active solution (colored sugar solution) and/or a quartz-plate with a vapor-deposited absorption layer.

In the following by means of the FIGS. 1 to 4 multiple optical measuring systems which are configured as polarimeter are described, by which a polarization rotation $\alpha_P(\lambda_0)$ of the measuring light which is caused by the sample at a standardized wavelength $\lambda_0$ can be determined, wherein systematic measuring errors are corrected and/or compensated which are caused by a wavelength-dependent absorption and/or transmission of the sample.

The described polarimeters respectively measure the optical activity of a substance, wherein the optical activity is the property of chemical compounds, in a solid state or in solution, to rotate the plane of polarized light when passing, by an amount which is characteristic for the respective compound (rotation value $\alpha$ of the polarization rotation). For determining the rotation value $\alpha$, the sample to be examined is brought between two polarization filters (so-called Nicol prisms, Glan-Thompson polarizers, Tourmaline plates or foil polarizers, Glan Taylor polarizers, dielectric polarization beam splitters, glass-based polarization filters, metal grating-polarizers etc.). The light which is sent out from a light source is polarized by a first polarization state generator (PSG), for example a polarization filter. If the polarization state analyzer (PSA), for example a polarization filter, is standing rotated by 90° with respect to the PSG, no light impinges on a detector. If the optically active substance is now brought between the PSG and the PSA, the optically active substance rotates the polarization direction of the passing light and it is required to rotate the PSA and/or the PSG by an angle, in order to achieve again that no light impinges on the detector. This rotation angle is proportional to the polarization-optical ability for rotation of the sample and/or substance to be examined and its concentration. Dependent on the embodiment, the light source may be integrated in the PSG and the detector or the detectors may be integrated in the PSA. The transferability of the invention from the subsequently as exemplary described concrete embodiments of a polarimeter to other types of polarimeters, for example such with rotating elements or multiple detectors is obvious for those skilled in the art.

FIG. 1 shows an optical measuring system which is configured as polarimeter 100 with two optical measuring channels. The polarimeter 100 comprises a light source L which sends out a measuring light ML along an analysis beam path. A polarization state generator PSG generates the polarized measuring beam and is radiating through the sample P to be examined which is located in the analysis beam path. After passing through the sample, the measuring light ML impinges on a polarization state analyzer PSA which is configured in a known manner such that it only allows that portion of measuring light ML to pass which comprises a certain polarization. The intensity of the measuring light ML which was let through by the polarization state analyzer PSA is captured by a detector Det.

It should be noted that an optical monochromator (not shown in the drawing) may be arranged in the analysis beam path, which serves for the spectrum of the measuring light ML which impinges on the sample P having a smaller bandwidth than the light which is directly emitted from the light source L.

According to the here illustrated embodiment, the polarization state generator PSG and/or the polarization state analyzer PSA may be rotated by a motor M1 and M2, respectively, until an optical rotation is compensated by an optically active sample P. The position of the polarization state generator PSG and/or the polarization state analyzer PSA is measured by at least one not illustrated angle measuring device (encoder) which is assigned to the at least one of the both motors M1, M2. The difference of a comparison angle with and without a sample P results in the optical rotation of the sample P.

Optionally, the polarization plane of the measuring light ML may be frequency-varied by a Faraday modulator FM and at the detector Det only signals with the same frequency may be detected and/or processed. Thereby, in a known manner disturbing influences, such as in particular scattering light, can be reduced or eliminated.

Typically, the sample P is located in a sample carrier PT which is exchangeably arranged in a sample container of the polarimeter 100. According to the illustrated embodiment, the sample P is a liquid sample and the sample carrier PT is a cuvette. The cuvette PT is transparent for the measuring light at least at its end faces which are perpendicular with respect to the optical axis of the measuring light ML. The cuvette may be also realized as flow-through cuvette.

In addition, according to the illustrated embodiment, also a temperature measurement of the sample P is performed by a temperature sensor TS which is principally known.

The polarization state of the measuring light ML which is rotated by the sample P is examined by the polarization state analyzer PSA which is arranged at an outlet of the cuvette and by the detector Det which ascertains at least an intensity of the measuring light ML. The results are supplied to an evaluation and control unit µP. The analysis may be performed for example by a defined rotation of the polarization state analyzer PSA with the motor M2. The regulation is performed on basis of the intensity value of the measuring light ML which is transmitted by the detector Det by a specification, for example of steps for a motor M2 which is configured as a step motor, for example. The evaluations of the evaluation and control unit µP are displayed on a display unit Dis.

It should be noted that diverse variants of this basic measuring principle are known in which the order of the elements which are radiated through may also be changed, where applicable.

For performing the analysis which is described in this document, in order to, by a direct measurement, correct the wavelength error of the optical rotation which results both from a wavelength-dependent transmission of the sample and from a rotation dispersion of the sample, the polarimeter 100 which is shown in FIG. 1 comprises two measuring channels which are assigned to two different wavelengths of measuring light ML. According to the here described embodiment, the respective wavelength is selected by a filter wheel 110 at which two interference filters 112 and 114 are mounted. For a fine adjustment of the interference filters 112 and 114, these may be also tilted in a not illustrated manner, such that the optical thickness of the respective interference filter 112, 114 is changing.

The filter wheel 110 may be rotated by an actuating motor 116, such that the interference filter 112 or 114, which is respectively assigned to the desired wavelength is located in the analysis beam path. Therefore, the polarimeter 100 is operated alternately with respectively one active measuring channel of the both measuring channels.

According to the here illustrated embodiment, the both measuring channels on the wavelength scale have a distance which is in a range between 0.1 nm and 20 nm. Within this range, small distances of, for example approximately 1 nm may be especially suitable. In contrast to known polarimeters, wavelength errors here are compensated. Therefore, it is not required anymore to meet the pre-given standardized wavelength as exactly as possible with an interference filter. Therefore, the interference filters 112, 114 do not mandatorily have to be adjusted by suitable tilting. Thereby, a significantly simpler construction of the filter wheel 110 without adjustment device for the tilting position of the interference filters 112, 114 is possible.

It should be noted that instead of the filter wheel 110, also a linearly slidable frame may be used at and/or in which the both interference filters 112, 114 are located.

The evaluation and control unit µP is adapted for performing the inventive method, in particular based on the above described explanation of the physical basics of the operation of a polarimeter with different wavelengths of measuring light.

Figure 2:
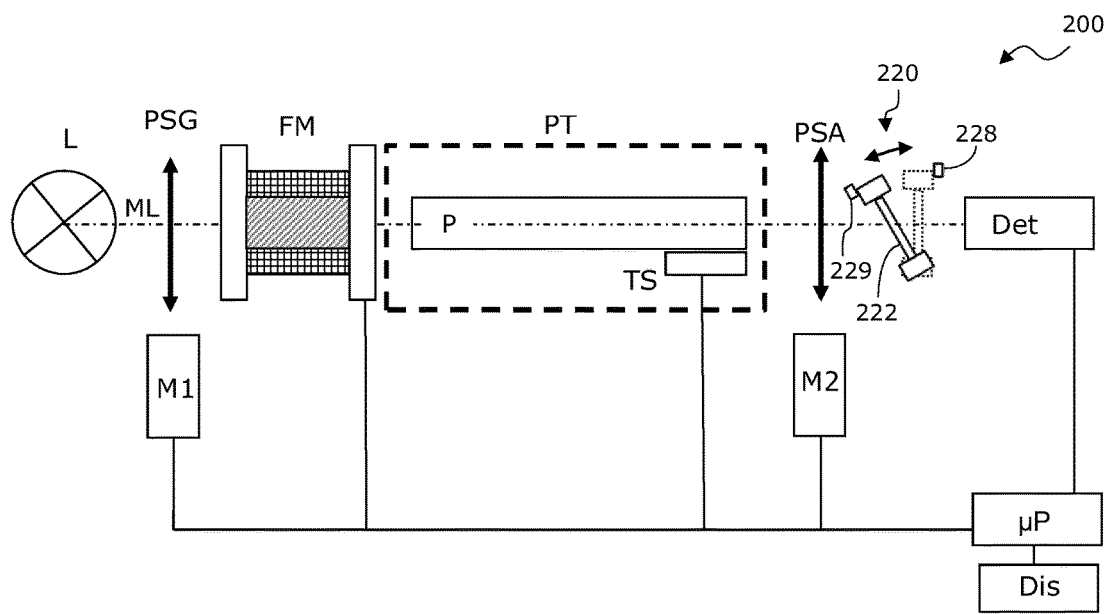
FIG. 2 shows a polarimeter, in which two measuring channels are realized by a tiltable interference filter.

FIG. 2 shows a polarimeter 200 which differs from the polarimeter 100 only in that the both measuring channels are realized by a tiltable filter holder 220 at which an interference filter 222 is attached. The filter holder 220 can be tilted from a first position which is shown dashed, which is exactly defined by a stop 228, into a second position whose exact angular position is determined by a stop 229. When tilting, the optical thickness of the interference filter 222 which is relevant for the measuring light ML is changing in a known manner, which in turn determines the wavelength which is let through by the interference filter 222.

It should be noted that the filter principles which are used for the both polarimeters 100 and 200 may also be combined. This in particular applies for the case that the respective polarimeter has more than two measuring channels. In this case, namely a rotatable filter wheel may be used in a simple manner, for example, which can be folded to two different stops by an actuator.

Figure 3:
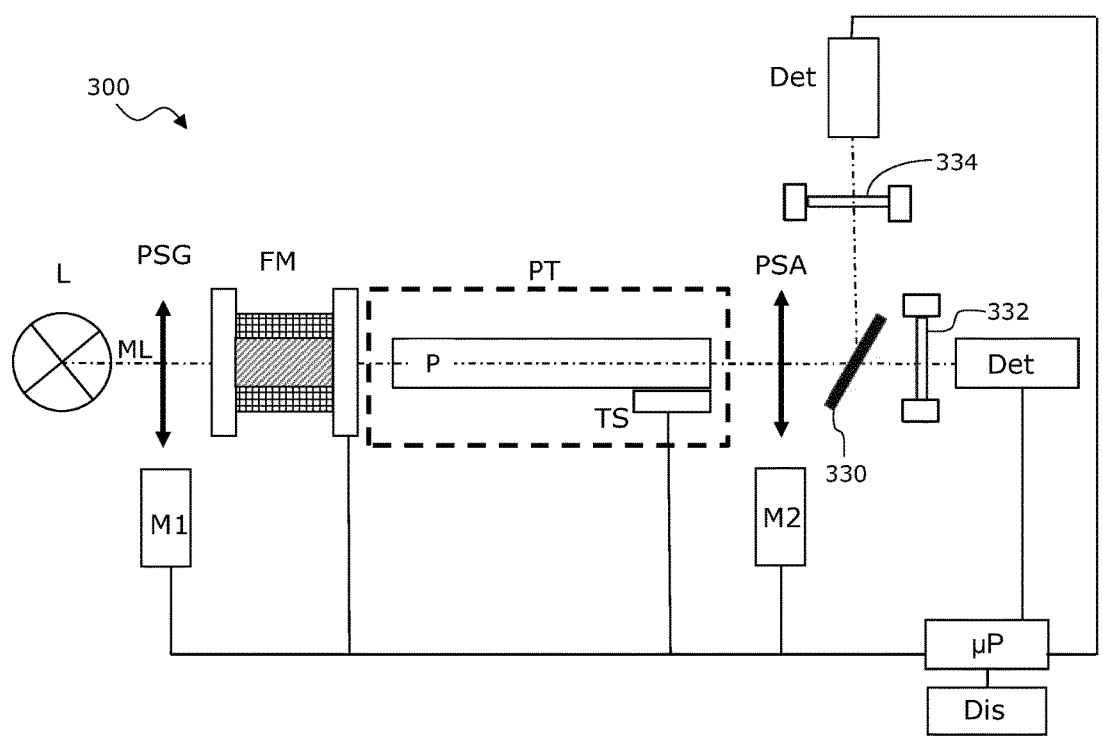
FIG. 3 shows a polarimeter, in which two measuring channels are spatially separated by a beam splitter.

FIG. 3 shows a polarimeter 300 in which two measuring channels are spatially separated by means of a beam splitter 330. This means that the measuring light ML after passing through the sample P is split in two partial beams. To each partial beam, an own wavelength selector 332 and 334, respectively, and an own detector Det is assigned. In this embodiment, the both measurements which are respectively assigned to one measuring channel can be performed simultaneously.

The beam splitter 330 may also be a polarization-dependent beam splitter. In this case, the polarization direction in the polarization state analyzer PSA has to be re-adjusted, if necessary, and the both measurements have to be performed subsequently to each other.

In further not illustrated embodiments, two wavelengths are realized by which the interference filters are radiated through by two partial beams in different angles simultaneously. Thereby, the measurements at both wavelengths can be performed simultaneously. These embodiments have the advantage that per standardized wavelength only one interference filter is required. They may be used both for one single standardized wavelength with a fixedly mounted interference filter and also for a polarimeter with multiple standardized wavelengths with exchangeable interference filters.

For example, a Wollaston prism can be used as polarization beam splitter, such that the beam is split in two partial beams which are divergent with respect to each other. At the outlet of the Wollaston prism, the partial beams are still so close together, that they both can commonly pass through an interference filter which is attached in close proximity. In a larger distance, the partial beams are separated so far that they can be mapped on two detectors. Here, multiple interference filters on a filter wheel are conceivable again. It is important that the interference filter is oriented such that both partial beams radiate through the interference filter with different angles, such that the partial beams have different wavelengths.

Furthermore, a normal beam splitter may be used and the one partial beam may be subsequently redirected, such that it intersects the first partial beam in the interference filter. Here, a variant with a single fixed interference filter and with two detectors or with two light-sensitive regions on an area detector is conceivable. When the beam splitter is polarization-sensitive, both measurements can be performed simultaneously.

Figure 4:
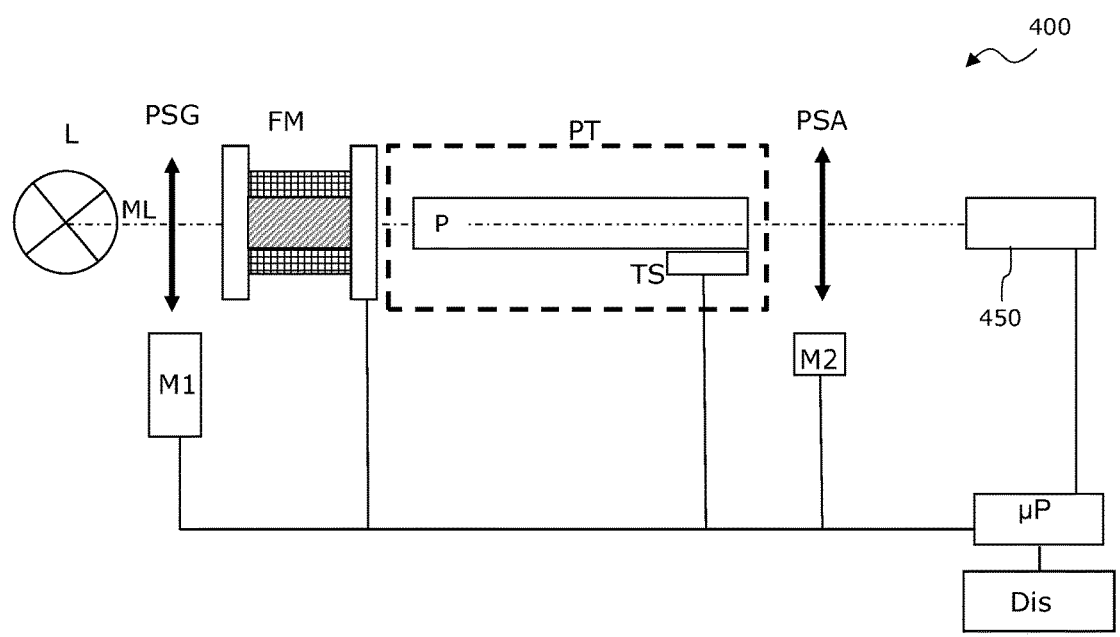
FIG. 4 shows a polarimeter, in which multiple measuring channels are realized by a spectrometer.

FIG. 4 shows a polarimeter 400 in which multiple measuring channels are realized by a spectrometer 450. A high measuring stability of the polarimeter 400 may be achieved if the spectrometer does not comprise movable components. Such a spectrometer may be a known monolithic array-spectrometer, for example, which allows a simultaneous measurement in different measuring channels which respectively are assigned to different wavelengths.

Suitable spectrometers 450 may be placed directly behind the polarization state analyzer PSA in the polarimeter 400, as illustrated in FIG. 4. This embodiment can be realized in an especially simple manner. It should only be noted that each wavelength channel and measuring channel, respectively, has an individual effective wavelength, an individual device function $G(\lambda)$ and an individual proportionality factor $\kappa$. The above described measurements of the relative transmission dispersion $T'/T$ and the optical rotation dispersion $\alpha'(\lambda_0)$ may be performed for each desired standardized wavelength in the spectral range which is covered by the spectrometer with two wavelengths-channels whose effective wavelengths are adjacent to the standardized wavelength $\lambda_0$.

If the measuring principle which is implemented in the polarimeter is reliant on an adjustment of the polarization state analyzer PSA and/or of the polarization state generator PSG, which adjustment is dependent on the value of the optical rotation $\alpha'(\lambda_0)$ of the sample (for example in a comparison of a polarizing filter to a dark position), the measurements for the selected standardized wavelengths have to be performed subsequently to each other. If the measuring principle which is implemented in the polarimeter is not reliant on an adjustment of the polarization state analyzer PSA and/or of the polarization state generator PSG, which adjustment is dependent on the value of the optical rotation $\alpha'(\lambda_0)$ of the sample, the measurements for the selected standardized wavelengths, or if desired, also for a complete spectrum can be performed simultaneously.

Subsequently, some components are described in more detail which can be used for embodiments of the invention in an advantageous manner.

As suitable light sources, besides thermal light sources (light bulbs), also light-emitting diodes, laser diodes, superluminescence-diodes, laser, broadband discharge lamps, narrowband discharge lamps, such as hollow-cathode lamps and in particular low-pressure-spectral lamps, can be used. If required, also wavelength converters can be used. Moreover, multiple light sources may be automatically or manually exchangeable or may be permanently (for example by wavelengths-selective elements) combined to a measuring beam. The measuring beam may further be prepared by diffusers or homogenizers and may be spatially guided by lenses or mirrors.

The polarization state generator (PSG) and the polarization state analyzer (PSA) may be configured according to diverse principles. PSGs and PSAs with fix, rotating or modulated polarization filters, retardation plates, polarization compensators and/or beam splitters may be used.

Dependent on the embodiment of the polarization state generator PSG, of the polarization state analyzer PSA and of the used evaluation algorithm, all or some elements of the so-called Müllermatrix of the sample can be determined as sample property. An example is the optical activity of the sample which is measured by the rotation of the polarization direction of linearly polarized light which is caused by the sample.

A simple possibility to compensate the polarization direction of the measuring light which is changed by the substance and to achieve the initial intensity values at the detector unit (the polarization state generator and the polarization state analyzer, after inserting the rotating substance, are preferably brought in a crossed position again which leads to minimum or no light passing) is a rotation of the polarization state generator or polarization state analyzer by means of a motor or a step motor.

A temperature from a temperature sensor and a light intensity which is received at the detector may be processed in the control and evaluation unit and the polarimeter may be regulated with it. The measurement of the rotational angle is regularly performed by an angle measuring device, typically an optical encoder, which is connected to the rotated optical element in a rigid manner. Alternatively, for lower accuracies, the steps which are moved by a step motor may be used for the angular measurement.

According to further embodiments, the rotation of the polarization plane which is caused by the optical activity of the sample can be compensated not by a mechanically movable element, but by a purely optical element, for example a Faraday-rotator. In a Faraday-rotator, the rotation of the polarization plane is proportional to the current through the coil of the Faraday-rotator. The current which is required for compensating the rotation which is caused by the sample is proportional to the ability for rotation of the substance and its concentration.

Regularly, the polarization properties of samples are dependent on the sample temperature as well. Thereby, the sample temperature can be measured by temperature sensors which immerse in the sample or are attached to the cuvette. In particular, photo multipliers, photodiodes, Avalanche-diodes, CCD-detectors, NMOS-detectors, CMOS-detectors and spectrometers are possible as detectors.

REFERENCE SIGNS 100 polarimeter
110 filter wheel
112 interference filter
114 interference filter
116 actuating motor
200 polarimeter
220 tiltable filter holder
222 interference filter
228 stop
229 stop 300 polarimeter
330 beam splitter
332 wavelength selector
334 wavelength selector
400 polarimeter
450 spectrometer
L light source
ML measuring light
PSG polarization state generator
FM Faraday modulator
PSA polarization state analyzer
µP evaluation and control unit
Det detector
M1 motor+angle measuring device
M2 motor+angle measuring device
TS temperature sensor
P sample
PT sample carrier/cuvette
Dis display unit

The invention claimed is:

1. An optical measuring system for determining polarization-optical properties of a sample, the optical measuring system comprising:
a polarization state generator which is configured for preparing a measuring light which is propagating along an analysis beam path with a defined polarization state;
a sample receptacle which is arranged downstream of the polarization state generator in the analysis beam path and which is adapted for receiving the sample;
a polarization state analyzer which is arranged downstream of the sample receptacle in the analysis beam path;
a detector which is arranged downstream of the polarization state analyzer in the analysis beam path, for detecting an intensity of the measuring light,
wherein the polarization state analyzer and the detector are configured for capturing a polarization rotation $\alpha_P(\lambda_{eff})$ of the measuring light which is caused by the sample; and
a processor for evaluating measuring signals from the detector,
wherein a wavelength-spectrum of the measuring light contains a first wavelength $\lambda_1$ and a second wavelength $\lambda_2$,
wherein the detector is configured for detecting measuring light with the first wavelength $\lambda_1$ separated from measuring light with the second wavelength $\lambda_2$, and
wherein the processor is configured for calculating a polarization rotation $\alpha_P(\lambda_0)$ of the measuring light which is caused by the sample at a standardized wavelength $\lambda_0$ in dependency from
(a) a first polarization rotation $\alpha_P(\lambda_1)$ at the first wavelength $\lambda_1$,
(b) a second polarization rotation $\alpha_P(\lambda_2)$ at the second wavelength $\lambda_2$,
(c) a first transmission characteristic $T(\lambda_1)$ of the sample at the first wavelength $\lambda_1$, and
(d) a second transmission characteristic $T(\lambda_2)$ of the sample at the second wavelength $\lambda_2$.

2. The optical measuring system of claim 1,
wherein the wavelength-spectrum of the measuring light further contains at least a third wavelength,
wherein the detector is configured for detecting measuring light with the third wavelength separated from measuring light with the second wavelength $\lambda_2$ and from measuring light with the first wavelength $\lambda_1$, and wherein the processor is further configured for calculating the polarization rotation $\alpha_P(\lambda_0)$ of the measuring light which is caused by the sample at the standardized wavelength $\lambda_0$, further in dependency from
a third polarization rotation at the third wavelength, and
a third transmission of the sample at the third wavelength.

3. The optical measuring system according to claim 1, further comprising:
a light source which is adapted for sending the measuring light along the analysis beam path.

4. The optical measuring system according to claim 1,
wherein a wavelength difference between the first wavelength $\lambda_1$ and the second wavelength $\lambda_2$ is smaller than 30 nm.

5. The optical measuring system according to claim 1,
wherein the processor is further configured for calculating the polarization rotation $\alpha_P(\lambda_0)$ of the measuring light which is caused by the sample at the standardized wavelength $\lambda_0$ based on
a first shift $\Delta\lambda_P(T')$ of a center-of-gravity-wavelength $\lambda_{eff}$ of the measuring light due to a wavelength-dependency of the transmission of measuring light through the sample,
a second shift $\Delta\lambda_G$ of the center-of-gravity-wavelength $\lambda_{eff}$ of the measuring light due to a wavelength-dependency of a transmission of measuring light through an entirety of the optical components of the optical measuring system and
the first polarization rotation $\alpha_P(\lambda_1)$ and the second polarization rotation $\alpha_P(\lambda_2)$.

6. The optical measuring system according to claim 1,
wherein the processor is further configured for calculating the polarization rotation $\alpha_P(\lambda_0)$ of the measuring light which is caused by the sample at the standardized wavelength $\lambda_0$, further based on
a polarization rotation $\alpha_P(\lambda_{eff})$ which is caused by the sample at an effective wavelength $\lambda_{eff}$ which is determined by optical properties of the entirety of the optical components of the optical measuring system and by the optical properties of the sample, and
an optical rotation dispersion $\alpha'_P(\lambda_0)$ which is caused by the sample and which is pre-known, at the standardized wavelength $\lambda_0$.

7. The optical measuring system according to claim 5,
wherein the optical rotation dispersion $\alpha'_P(\lambda_0)$ which is caused by the sample at the standardized wavelength $\lambda_0$ is determined by the quotient of
(a) a difference between the first polarization rotation $\alpha_P(\lambda_1)$ and the second polarization rotation $\alpha_P(\lambda_2)$ and
(b) a wavelength difference between the first wavelength $\lambda_1$ and the second wavelength $\lambda_2$.

8. The optical measuring system according to claim 5,
wherein the processor is further configured for determining the first shift $\Delta\lambda_P(T')$ based on a relative transmission dispersion $T'/T$ of the sample and a proportionality factor $\kappa$,
wherein the relative transmission dispersion $T'/T$ of the sample is given by a quotient of the transmission dispersion $T'$ of the sample and the transmission $T$ of the sample and the proportionality factor $\kappa$ is specific for the transmission dispersion of the entirety of the optical components and is determinable by an optical calibration of the optical measuring system using a reference sample.

9. The optical measuring system of claim 8,
wherein the relative transmission dispersion $T'/T$ of the sample is determined by the quotient of (a) a difference between the first transmission characteristic $T(\lambda_1)$ and the second transmission characteristic $T(\lambda_2)$ and (b) a product of (b1) a sum of the first transmission characteristic $T(\lambda_1)$ and the second transmission characteristic $T(\lambda_2)$ and (b2) a wavelength difference between the first wavelength $\lambda_1$ and the second wavelength $\lambda_2$.

10. The optical measuring system according to claim 1, further comprising:

a switchable optical filter device which is located in the analysis beam path and which is adapted for determining an operational state of the optical measuring system to the effect that in a first operational state only measuring light with the first wavelength $\lambda_1$ and in a second operational state only measuring light with the second wavelength $\lambda_2$ reaches the detector.

11. The optical measuring system according to claim 10, wherein the switchable optical filter device comprises a first optical filter which is assigned to the first wavelength λ1 and a second optical filter which is assigned to the second wavelength λ2, and wherein the switchable optical filter device is configured for arranging the first optical filter in the analysis beam path in the first operational state and for arranging the second optical filter in the analysis beam path in the second operational state.

12. The optical measuring system according to claim 10, wherein the switchable optical filter device comprises an optical filter which is arranged in the analysis beam path, and an actuator which is adapted for varying an angular position of the optical filter between a first angle which is assigned to the first operational state and a second angle which is assigned to the second operational state.

13. The optical measuring system according to claim 1, further comprising:

a beam splitter which is arranged downstream of the sample in the analysis beam path and which is configured for splitting the measuring light into a first partial beam and into a second partial beam, wherein the first partial beam is assigned to the first wavelength $\lambda_1$ and the second partial beam is assigned to the second wavelength $\lambda_2$, wherein the detector comprises two detector elements, wherein a first detector element is assigned to the first wavelength $\lambda_1$ and the second detector element is assigned to the second wavelength $\lambda_2$.

14. The optical measuring system according to claim 1, wherein the detector forms at least a part of a spectrometer.

15. A method of determining polarization-optical properties of a sample, the method comprising:

preparing, by a polarization state generator, a measuring light which is propagating along an analysis beam path with a defined polarization state;

directing the measuring light to a sample which is located downstream of the polarization state generator in the analysis beam path;

capturing a polarization rotation $\alpha_P(\lambda_{eff})$ of the measuring light which is caused by the sample (i) by a polarization state analyzer which is arranged downstream of the sample in the analysis beam path, and (ii) by a detector which is arranged downstream of the polarization state analyzer in the analysis beam path, wherein a wavelength-spectrum of the measuring light contains at least a first wavelength $\lambda_1$ and a second wavelength $\lambda_2$ and wherein the detector is detecting measuring light with the first wavelength $\lambda_1$ separated from measuring light with the second wavelength $\lambda_2$; and evaluating measuring signals from the detector by a processor, wherein a polarization rotation $\alpha_P(\lambda_0)$ of the measuring light which is caused by the sample at a standardized wavelength $\lambda_0$ is calculated in dependency from (a) a first polarization rotation $\alpha_P(\lambda_1)$ and a first wavelength $\lambda_1$, (b) a second polarization rotation $\alpha_P(\lambda_2)$ at the second wavelength $\lambda_2$, (c) a first transmission characteristic $T(\lambda_1)$ of the sample at the first wavelength $\lambda_1$, and (d) a second transmission characteristic $T(\lambda_2)$ of the sampling at the second wavelength $\lambda_2$.

16. The method of claim 15, further comprising:

determining the first transmission characteristic $T(\lambda_1)$ by a comparison of a first intensity which is measured by the detector and a further first intensity which is measured by the detector, wherein the first intensity results from a measurement without a sample and the further first intensity results from a measurement with the sample; and determining the second transmission characteristic $T(\lambda_2)$ by a comparison of a second intensity which is measured by the detector and a further second intensity which is measured by the detector, wherein the second intensity results from a measurement without a sample and the further second intensity results from a measurement with the sample.

17. The method of claim 16, further comprising:

determining the first polarization rotation $\alpha_P(\lambda_1)$ by a comparison between a captured first polarization state and a captured further first polarization state, wherein the first polarization state results from a measurement without a sample and the further first polarization state results from a measurement with the sample; and determining the second polarization rotation $\alpha_P(\lambda_2)$ by a comparison between a captured second polarization state and a captured further second polarization state, wherein the second polarization state results from a measurement without a sample and the further second polarization state results from a measurement with the sample.

18. A non-transitory computer program for determining polarization-optical properties of a sample, wherein the computer program, when it is executed by a processor (μP), in connection with a polarization state generator (PSG), a sample receptacle (PT), a polarization state analyzer (PSA) and a detector (Det) is adapted for generating a measuring light with a defined polarization state;

directing the measuring light to a sample located downstream of the polarization state generator in an analysis beam path;

capturing a polarization rotation of the measuring light with a polarization state analyzer arranged downstream of the sample in the analysis beam path, and a detector arranged downstream of the polarization state analyzer in the analysis beam path, wherein a wavelength-spectrum of the measuring light contains at least a first wavelength and a second wavelength, wherein the detector is detecting measuring light with the first wavelength separated from measuring light with the second wavelength; and evaluating signals from the detector with the processor, wherein a polarization rotation of the measuring light caused by the sample at a standardized wavelength is determined from (a) a first polarization rotation at the first wavelength,
(b) a second polarization rotation at the second wavelength,
(c) a first transmission characteristic of the sample at the first wavelength, and
(d) a second transmission characteristic of the sample at the second wavelength.

* * * * *